(12) United States Patent
Dogramadzi et al.

(10) Patent No.: US 11,090,013 B2
(45) Date of Patent: Aug. 17, 2021

(54) DEVICE FOR PATIENT MONITORING

(71) Applicants: UNIVERSITY OF THE WEST OF ENGLAND, BRISTOL, Bristol (GB); TAUNTON AND SOMERSET NHS TRUST, Somerset (GB)

(72) Inventors: Sanja Dogramadzi, Bristol (GB); Simon Goldsworthy, Somerset (GB)

(73) Assignees: UNIVERSITY OF THE WEST OF ENGLAND, BRISTOL, Bristol (GB); TAUNTON AND SOMERSET NHS TRUST, Somerset (GB)

( * ) Notice: Subject to any disclaimer, the term of this patent is extended or adjusted under 35 U.S.C. 154(b) by 339 days.

(21) Appl. No.: 16/303,634

(22) PCT Filed: May 19, 2017

(86) PCT No.: PCT/EP2017/062149
§ 371 (c)(1),
(2) Date: Nov. 20, 2018

(87) PCT Pub. No.: WO2017/202725
PCT Pub. Date: Nov. 30, 2017

(65) Prior Publication Data
US 2020/0138387 A1    May 7, 2020

(30) Foreign Application Priority Data
May 23, 2016    (GB) ..................... 1609040

(51) Int. Cl.
*A61N 5/00* (2006.01)
*A61B 6/04* (2006.01)
*A61N 5/10* (2006.01)

(52) U.S. Cl.
CPC .......... *A61B 6/0492* (2013.01); *A61N 5/1049* (2013.01); *A61N 2005/1057* (2013.01)

(58) Field of Classification Search
CPC .......... A61N 6/0429; A61N 2005/1057; A61N 5/1049; A61B 5/1127
See application file for complete search history.

(56) References Cited

U.S. PATENT DOCUMENTS

| 5,727,554 A | 3/1998 | Kalend et al. |
| 2008/0031414 A1 | 2/2008 | Coppens |

(Continued)

FOREIGN PATENT DOCUMENTS

| WO | 03/003796 A1 | 1/2003 |
| WO | 2015/149044 A1 | 10/2015 |

OTHER PUBLICATIONS

GB Search Report issued by the GB IPO in GB Application No. GB1609040.9, dated Nov. 16, 2016, 3 pgs.
(Continued)

*Primary Examiner* — Dani Fox
(74) *Attorney, Agent, or Firm* — Troutman Pepper Hamilton Sanders LLP

(57) ABSTRACT

A movement detection device for detecting quantitatively the movement of a patient by capturing images of a deformable surface having an indicator associated therewith, the indicator being responsive to changes in a profile of the deformable surface. The captured images are analysed to derive a patient movement from the changes in the profile of the deformable surface. For example, the movement detection device of the invention can detect the sense (translational and/or rotational) and magnitude of the patient movement. This information may enable real time adjustment of the treatment signal or indeed provide a safety facility whereby should there be detection that the patent has moved or has moved beyond certain parameters, the device that is observing or treating the patent is switched off.

16 Claims, 2 Drawing Sheets

(56) References Cited

U.S. PATENT DOCUMENTS

2009/0129556 A1* 5/2009 Ahn .................. A61B 6/04
378/208
2011/0317890 A1 12/2011 Baroni et al.

OTHER PUBLICATIONS

International Search Report and Written Opinion issued by the International Searching Authority in International Application No. PCT/EP2017/062149, dated Aug. 10, 2017, 13 pgs.

* cited by examiner

DEVICE FOR PATIENT MONITORING

CROSS-REFERENCE TO RELATED APPLICATIONS

This application is a U.S. National Phase of International Patent Application No. PCT/EP2017/062149, filed on May 19, 2017, which published as WO2017/202725 A1 on Nov. 30, 2017, and claims priority to GB Patent Application No. 1609040.9, filed on May 23, 2016, all of which are herein incorporated by reference in their entirety.

FIELD OF THE INVENTION

The invention relates to a patient monitoring device for use, in particular but not exclusively, during radiotherapy or other medical procedures where it is necessary for the position of the patient to be accurately known. In particular, the invention relates to a movement detection device that can track the motion of a patient, e.g. a patient's head, so that treatment radiation can be targeted accurately.

BACKGROUND TO THE INVENTION

To ensure patients are in a fixed position during diagnosis or treatment, they are usually immobilised in a thermoplastic mask for head and neck radiotherapy. A thermoplastic mask does not adapt to contour changes such as weight loss and can be an uncomfortable experience for patients.

WO 2013/107472 discloses a radiotherapy apparatus in which the position of a patient is held in a set location and the patient is monitored by optical cameras during treatment. Any detected change in position causes the treatment to be interrupted so that the treatment signal can be repositioned.

SUMMARY OF THE INVENTION

At its most general, the present invention provides a movement detection device for detecting quantitatively the movement of a patient. For example, the movement detection device of the invention can detect the sense (translational and/or rotational) and magnitude of the patient movement. This information may enable real time adjustment of the treatment signal or indeed provide a safety facility whereby should there be detection that the patent has moved or has moved beyond certain parameters, the device that is observing or treating the patent is switched off.

The invention may be used instead of conventional immobilisation devices. The invention may thus improve patient comfort whilst retaining the accuracy, speed and safety of treatment.

According to the invention there is provided device for detecting patient movement whilst undergoing a medical process, the device comprising: a deformable surface; an indicator associated with the deformable surface, the indicator being responsive to changes in a profile of the deformable surface; an imaging device arranged to capture images of the indicator; and a processor arranged to: analyse the captured images to determine changes in the profile of the deformable surface, derive a patient movement from the determined changes in the profile of the deformable surface, and output information indicative of the derived patient movement, wherein the derived patient movement comprises a type and magnitude of motion. By providing an indicator that is responsive to changes in the profile of the deformable surface, the device can distinguish between different types of movement based on the different ways in which the indicator responds upon deformation of the deformable surface The indicator may provide a visible indication of a plurality of points on the deformable surface. For example, it may be an array of markers on the deformable surface, or a grid whose shape depends on the profile of the surface.

The output information may be displayed to an operator (i.e. clinician), e.g. on a suitable user interface. The output information may be displayed in a graphical and/or numerical format.

By monitoring how a magnitude in the change of the indicator, e.g. how much markers in the array move within the captured images, a magnitude for the motion can also be derived.

The deformable surface may be a resiliently deformable body, e.g. made from silicone rubber or the like. The deformable surface may have an upper side for contact with the patient. The indicator may be arranged on an underside of the deformable surface, e.g. beneath the upper side. The imaging device may thus be located beneath the deformable surface, e.g. on the opposite side to the patient.

The indicator may have a contrasting appearance relative to surrounding parts of the deformable surface. For example, it (or each marker in the array of markers) may be reflective or coloured differently. In one example, the underside of the deformable surface may be black and the indicator or markers may be white. This arrangement may work well for an imaging device that operates in the visible part of the spectrum. However, the invention need not be limited to this; the imaging device may operate in other parts of the spectrum (e.g. infrared), and the markers may be adapted accordingly.

If the indicator comprises an array of markers, the array of markers may comprise a regular matrix of discrete spots formed or mounted on the deformable surface when in a rest state. Deformation of the deformable surface thus distorts the regular matrix. These distortions can be analysed to derive the movement.

In one example, the array of markers may comprise a plurality of pins protruding from the deformable surface. The pins may be integrally formed with the deformed surface, e.g. moulded in a single piece of material (e.g. silicone rubber).

The derived patient movement may comprise data indicative of magnitude of translational movement in three orthogonal directions. The three orthogonal directions may include two orthogonal directions across a plane of the deformable surface and one direction normal to that plane.

The derived patient movement may comprise data indicative of magnitude of rotational movement in two degrees of freedom with respect to the deformable surface. The rotational movement may be indicative of an object rolling across the deformable surface in two orthogonal directions. This may correspond to the roll and pitch of a patient's head resting on the deformable surface, for example.

The processor may be further arranged to compare the magnitude or sense of derived patient movement with a predetermined threshold, wherein the output information is indicative of whether or not that threshold is exceeded. In this way, the device may be used as a trigger to warn if patient movement has exceeded a desirable or safe tolerance.

The deformable surface may be mounted on a patient bed for use with a treatment apparatus, e.g. a radiotherapy apparatus or any other system in which a directional energy beam is used to treat, image or otherwise operatively interact with a patient's body. The deformable surface may form a patient support e.g. a pillow or a mattress for the surface that the patient is lying on e.g., a patient bed.

The imaging device may be mounted under the patient bed, e.g. with the underside of the deformable surface within its field of view. An aperture may be formed in the patient bed to enable the imaging device to see the array of markers.

The imaging device may be a webcam or other camera in wireless communication with the processor. The imaging device may comprise a fiberscope or other compact fibre-optic based imaging device.

In another aspect, the invention provides an apparatus for medical imaging or treatment comprising: a device having a gantry for emitting a signal for treating or imaging a patient; a patient bed for locating under the gantry; a controller arranged to control the direction of the signal; and a patient movement detection device as described above on the patient bed, wherein the controller is arranged to receive the output information from the device and to control the signal based on the output information. In one example, the controller may be arranged to control the direction of the signal, e.g. to maintain a relative position between the patient and the signal. In another example, the controller may be arranged to switch off or otherwise adapt the signal upon detecting patient movement beyond a certain threshold. The apparatus may be a radiotherapy apparatus, in which the gantry emits a signal for treating, e.g. ablating or otherwise thermally exciting, biological tissue.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Figure 1:
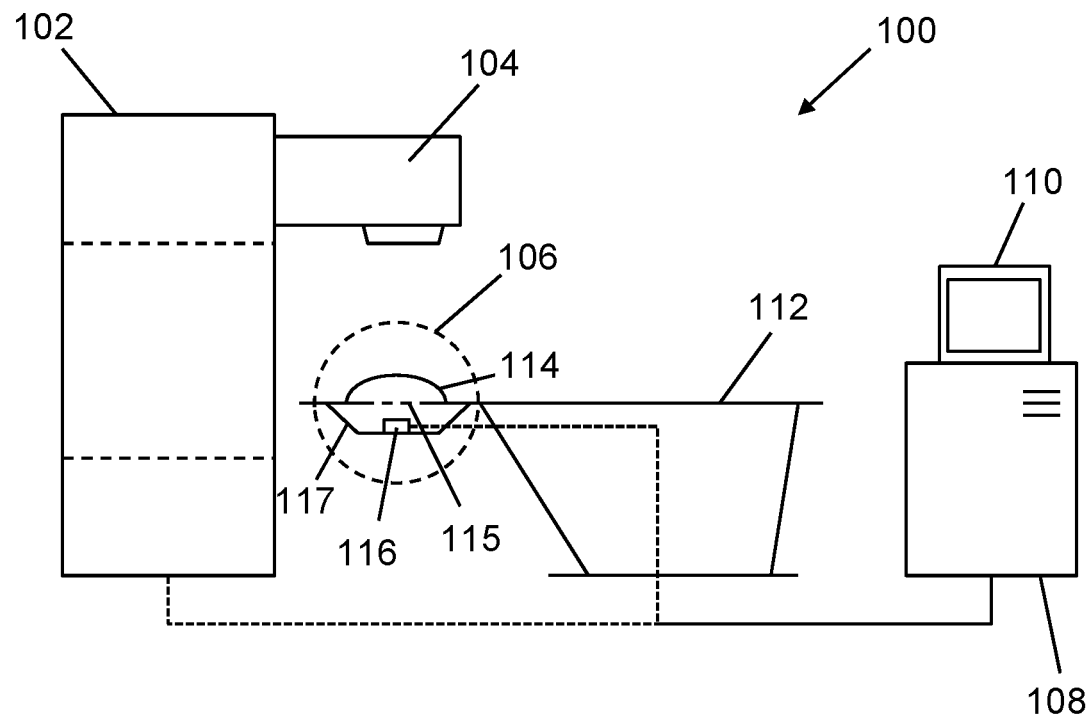
FIG. 1 is a schematic side view of a radiotherapy apparatus which incorporates a movement detection device that is an embodiment of the invention.

FIG. 1 shows a radiotherapy apparatus 100 that incorporates a movement detection device that is an embodiment of the invention. The radiotherapy apparatus 100 comprises a linear accelerator 102 that has a movable gantry 104 protruding therefrom to overhang a portion of a patient couch 112. The linear accelerator is in communication with a controller 108, which comprises a user interface (not shown) and a display 110. As is conventional, the linear accelerator can be operated by a user from the controller 108.

In this embodiment, the radiotherapy apparatus comprises a movement detection device 106 that is mounted on or integrated with the patient bed 112 in a region that can be located under the gantry 104. The movement detection device 106 comprises a deformable surface 114, which in this embodiment is in the form of a pillow for receiving a patient's head. An aperture 115 is formed through the patient bed 112 in a region underneath the deformable surface 114 so that the underside of the deformable surface 114 is visible from beneath the patient bed 112. In this embodiment, the movement detection device 106 includes a camera 116 that is mounted beneath the patient bed 112 in a manner such that the underside of the deformable surface 114 is within the field of view of the camera 116. A mounting frame 117 may be affixed to the underside of the patient bed 112 to support the camera 116 in a suitable position.

The camera 116 may be any suitable imaging device, e.g. webcam, etc. The camera 116 is in communication with the controller 108 (e.g. wired or wirelessly) to transmit captured images of the underside of the deformable surface for processing in the controller 108. The captured images are processed to determine movement of the patient's head during treatment. In this embodiment, it is anticipated that processing of the images from the camera 116 will take place in the controller. However, in other embodiments, the processing may occur separately, e.g. on a suitable processing device mounted together with the camera 116 on the frame 117. In this arrangement, the movement detection device may be arranged to communicate information indicative of a patient's movement directly to the controller 108.

In use, the patient head movement that is detected using the images captured by the camera 116 can be used by the controller 108 to fine tune the position of the gantry and/or treatment radiation transmitted from the gantry 104 in order to ensure accurate treatment of a desired region in the patient without unnecessarily constraining the patient's ability to move.

Figure 2:
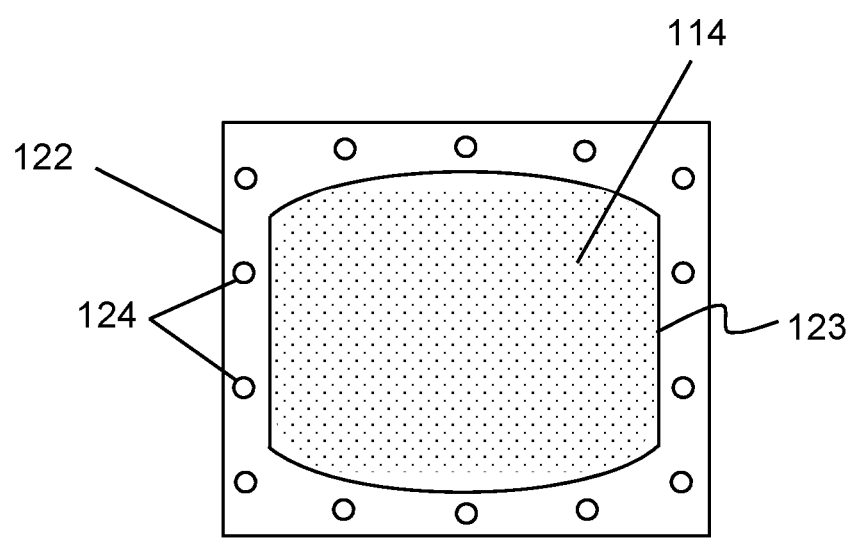
FIG. 2 is a schematic view of the underside of a movement detection device that is an embodiment of the invention.

FIG. 2 is a schematic view of the underside of the deformable surface 114 shown in FIG. 1, e.g. as seen from the point of view of the camera 116. The underside of the deformable surface comprises an array of markers (seen as an array of dots in FIG. 2) attached to or formed integrally with the deformable surface 114. Thus, as the deformable surface 114 changes shape due to movement of a patient's head, the position of the markers with respect to one another varies in a manner that enables the nature of the movement to be determined.

The deformable surface is mounted on a frame 122, which in turn may be attached to or formed as part of the patient bed 112. The frame defines an aperture which may be or be aligned with the aperture 115 discussed above.

In this embodiment, a series of light sources 124 are mounted around the frame 112 to illuminate the underside of the deformable surface 114. It may be desirable for the deformable surface to be illuminated in a uniform manner from all directions, so the light sources may be equally spaced around the periphery of the aperture 123. Any suitable light source can be used, e.g. LED, halogen bulb, etc.

The markers on the underside of the deformable surface are preferably arranged in a regularly spaced array of discrete points, e.g. spots, dots, or any other geometrical shape capable of defining a spatial point. The markers preferably have a contrasting appearance with respect to the remainder of the underside of the deformable surface. For example, the deformable surface may be black, whereas the markers may be coloured or reflective so that their position is easily seen.

Figure 3:
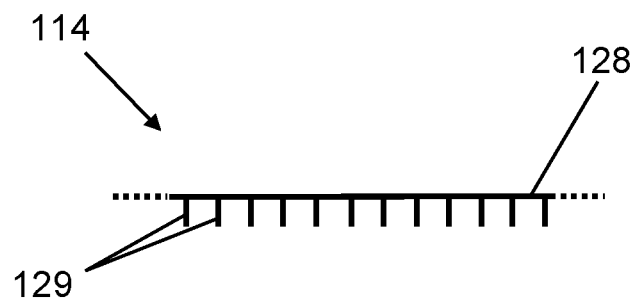
FIG. 3 is a schematic cross-sectional view through part of a deformable surface that can be used in the movement detection device shown in FIG. 2.

FIG. 3 shows an example of how the markers may be provided in one embodiment of the invention. FIG. 3 shows a schematic cross section through part of the deformable surface 114. Here it can be seen that the deformable surface 114 is formed from a skin 128 that has plurality of pin-like protuberances 129 extending from the underside thereof. The skin 128 and protuberances 129 may be moulded in one piece, e.g. from silicone rubber or the like. The protuberances 129 may be referred to as papillae pins. The pins 129 are arranged to extend in a direction normal to the plane of the skin 128. The height of the pins is selected so that they contain this orthogonal disposition even when the skin 128 deforms. The markers may be provided on the tips of the pins 129, e.g. by making them a different colour from the rest of the material used to make the deformable surface 114.

The number of markers provided on the underside of the deformable surface 114 can be selected in accordance with the desired resolution of movements to be detected. Movement of the markers is assessed by comparing images captured by the camera and determining movement of markers, e.g. in terms of pixel displacement across the image. When the array is considered as a whole, different patterns of marker movement within the array are indicative of different types of movement.

In order to derive the type and magnitude of movement from changes in the array of markers, a training set of data is obtained that includes both patient positional data (e.g. indicative of head position) taken over a period of time during which the patient moves over the deformable surface and concurrently obtained marker position data (e.g. indicative of the displacement between markers or between markers and an initial position). The marker position data can be obtained from images of the array of markers obtained at the same time as the patient positional data. Using machine learning techniques, e.g. training one or more classifiers using the training set of data, it is possible to distinguish different types of patient movement in real time on the basis of marker position data alone.

In use, the movement detection device can be configured to detect five basic movements of a patient's head on the deformable surface. The device may detect three types of translational movement: two translations across the pillow—laterally (x-axis) and longitudinally (y-axis), and one translation orthogonal to the surface of the patient bed 112, i.e. vertically (z-axis) relative to the deformable surface. In addition, the movement detection device can detect two rotational movements of the patient's head: roll and pitch. The movement device therefore can be used as a three-dimensional head position tracking monitor. The markers on the underside of the deformable surface create and image comprising a matrix of dots that can be captured by the camera. By tracking how the pattern of dots varies through a sequence of images captured by the camera, values for the magnitude of the each of the five movements discussed above can be obtained.

To verify this feasibility of the present invention, tracking data obtained from variations in the marker pattern across a series of images was compared concurrently obtained head position data captured by a Polaris (MDI) system that had a tracking tool attached to the patient's mouth. This test demonstrated that, even with relatively wide spacing between the markers, the movement detection device of the invention is capable of achieving clinically useful values for resolution and repeatability.

The movement detection device of the invention may find use as a replacement for the currently used rigid masks or braces that operate by immobilising a patient's head and neck during radiotherapy. This type of rigid device does not adapt to contour changes that can occur due to weight loss, and are often a cause of patient discomfort. The present invention may provide a more comfortable experience, whilst still enabling the radiotherapy apparatus to accurately target the desired treatment region.

Figure 4:
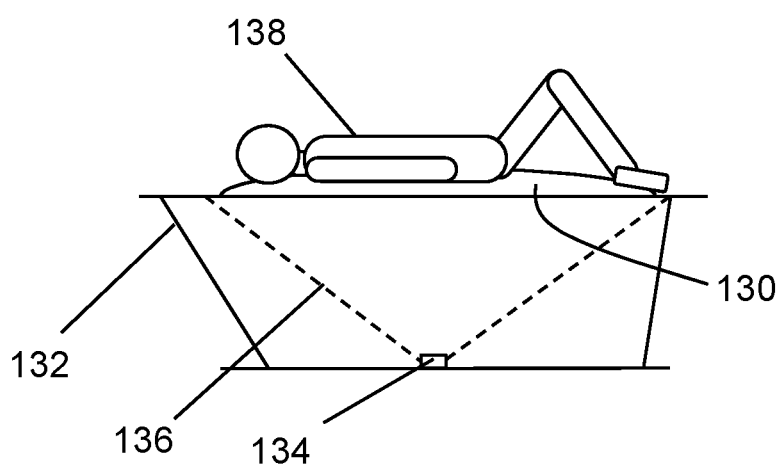
FIG. 4 shows a schematic side view of a patient couch that incorporates a movement detection device that is another embodiment of the invention.

FIG. 4 shows a movement detection device that is another embodiment of the invention. In this case, the deformable surface 130 that is formed on a patient bed 132 to receive the whole body of a patient 138. In this example, the imaging device (e.g. camera) 134 may be mounted on the base of the patient bed 132 so that its field of view 136 can encompass the entire underside of the mattress 130.

The above general disclosure and description of specific embodiments will make available to one skilled in the relevant art further adaptations and modifications which fall within the general concept of the present invention. Such adaptations and modifications may include combinations of features presented in different embodiments described above, and such combinations are to be considered as expressly disclosed herein.

While various embodiments of the present invention have been described above, it should be understood that they have been presented by way of example, and not limitation. It would be apparent to one skilled in the relevant art(s) that various changes in form and detail could be made therein without departing from the scope of the invention as defined in the claims.

The invention claimed is:

1. A device for detecting patient movement whilst undergoing a medical process, the device comprising:
   a deformable surface;
   an indicator associated with the deformable surface, the indicator being responsive to changes in a profile of the deformable surface;
   an imaging device arranged to capture images of the indicator; and
   a processor arranged to:
   analyse the captured images to determine changes in the profile of the deformable surface,
   derive a patient movement from the determined changes in the profile of the deformable surface, and
   output information indicative of the derived patient movement,
   wherein the derived patient movement comprises a type and magnitude of motion,
   wherein the indicator comprises an array of markers on the deformable surface.

2. A device according to claim 1, wherein the indicator provides a visible indication of a plurality of points on the deformable surface.

3. A device according to claim 1, wherein the array of markers comprises a regular matrix of discrete spots.

4. A device according to claim 1, wherein the array of markers comprises a plurality of pins protruding from the deformable surface.

5. A device according to claim 1, wherein the deformable surface has an upper side for contact with the patient, and wherein the indicator is arranged on an underside of the deformable surface, beneath the upper side.

6. A device according to claim 1, wherein the indicator has a contrasting appearance relative to surrounding parts of the deformable surface.

7. A device according to claim 1, wherein the derived patient movement comprises data indicative of magnitude of translational movement in three orthogonal directions.

8. A device according to claim 1, wherein the derived patient movement comprises data indicative of magnitude of rotational movement in two degrees of freedom with respect to the deformable surface.

9. A device according to claim 1, wherein the deformable surface is mounted on a patient bed for use with a radiotherapy apparatus.

10. A device according to claim 9, wherein the deformable surface forms a pillow for the patient bed.

11. A device according to claim 9, wherein the deformable surface forms a mattress for the patient bed.

12. A device according to claim 9, wherein the imaging device is mounted under the patient bed.

13. A device according to claim 9, wherein the imaging device is a webcam in wireless communication with the processor.

14. An apparatus for medical imaging or treatment, the apparatus comprising:
   a device having a gantry for emitting a signal for treating or imaging a patient;
   a patient bed for locating under the gantry;
   a controller arranged to control the direction of the signal; and
   a patient movement detection device according to any preceding claim on the patient bed, wherein the controller is arranged to receive the output information from the device and to control the signal based on the output information.

15. An apparatus according to claim 14, wherein the controller is arranged to control the direction of the signal based on the output information.

16. An apparatus according to claim 14, wherein the controller is arranged to switch off or otherwise adapt the signal in the output information is indicative of patient movement beyond a certain threshold.

\* \* \* \* \*